(12) United States Patent
de Nanteuil et al.

(10) Patent No.: US 6,339,092 B1
(45) Date of Patent: Jan. 15, 2002

(54) METALLOPROTEASE INHIBITORS

(75) Inventors: Guillaume de Nanteuil, Suresnes; Alain Benoist, Franconville; Jacqueline Bonnet, Paris; Massimo Sabatini, Garches; Ghanem Atassi, Saint Cloud; Alain Pierre, Les Alluets le Roi, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/608,240

(22) Filed: Jun. 30, 2000

(30) Foreign Application Priority Data

Jul. 1, 1999 (FR) .............................. 99 08448

(51) Int. Cl.$^7$ ................. A61K 31/435; C07D 491/048
(52) U.S. Cl. ................. 514/302; 540/597; 544/127; 544/233; 546/115; 546/116
(58) Field of Search ................. 546/115, 116; 514/302; 540/597; 544/127, 333

(56) References Cited

U.S. PATENT DOCUMENTS 5,866,587 A * 2/1999 De Nanteuil et al. ....... 514/302

* cited by examiner

*Primary Examiner*—Bernard Dentz
(74) *Attorney, Agent, or Firm*—The Firm of Hueschen and Sage; G. Patrick Sage

(57) ABSTRACT

A compound selected from those of the formula (I):

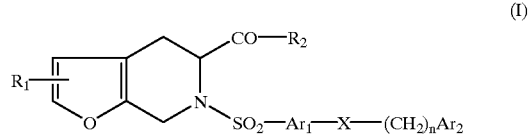

(I)

wherein:

$R_1$ represents hydrogen or halogen, or alkyl or alkoxy, $R_2$ represents hydroxy, alkoxy or —NHOH, $Ar_1$ represents phenylene or biphenylene, X represents oxygen or sulphur, NR, —C≡C— or a bond, R represents hydrogen or alkyl, n is an integer from 0 to 6 inclusive, $Ar_2$ represents any one of the groups as defined in the description, its isomers and addition salts thereof with a pharmaceutically-acceptable acid or base, and medicinal products containing the same which are useful as metalloprotease inhibitors.

15 Claims, No Drawings

METALLOPROTEASE INHIBITORS

FIELD OF THE INVENTION

The present invention relates to new metalloprotease inhibitors and to pharmaceutical compositions containing them.

In the physiological state, the synthesis of connective tissues is in dynamic equilibrium with the degradation of the extracellular matrix. That degradation is due to zinc proteases (metalloproteases) secreted by the cells of the existing matrix: they are, without implying any limitation, collagenases (MMP-1, MMP-8, MMP-13), gelatinases or collagenases of type IV (MMP-2, MMP-9) and stromelysins (MMP-3).

In the normal state, those catabolic enzymes are regulated in terms of their synthesis and their secretion, and in terms of their extracellular enzymatic activity, by natural inhibitors, such as $\alpha_2$-macroglobulin or the TIMPs (Tissue Inhibitors of MetalloProteinases), which form inactive complexes with the metalloproteases.

A common factor in pathologies in which those enzymes are implicated is an imbalance between the activity of the activated enzymes and that of their natural inhibitors, the consequence of which is excessive tissue degradation.

Uncontrolled and accelerated membrane degradation by resorption of the extracellular matrix catalysed by the metalloproteases is a parameter common to a number of pathological conditions, such as rheumatoid arthritis, arthrosis, tumour invasion and growth, including malignant spread and the formation of metastases, ulcerations, atherosclerosis, etc.

BB94, a metalloprotease inhibitor, has recently exhibited anti-tumour activity in clinical use, where it has proved to be active against ovarian cancers (Becket el al., DDT 1996. 1 (1), 16).

It may therefore be expected that a metalloprotease inhibitor will restore the equilibrium between protease and inhibitor and thus favourably modify the development of such pathologies.

A certain number of metalloprotease inhibitors have been described in the literature. There should be mentioned, more especially, the compounds described in Patent Specifications WO 95/35275, WO 95/35276, EP 606 046, WO 96/00214 and EP 803 505.

The compounds of the present invention are not only new but have also proved to be more powerful metalloprotease inhibitors than those described in the literature, thus making them potentially useful in the treatment of cancer, rheumatic diseases, such as arthrosis and rheumatoid arthritis, atherosclerosis, etc.

DETAILED DESCRIPTION OF THE INVENTION

More specifically, the present invention relates to compounds of formula (I):

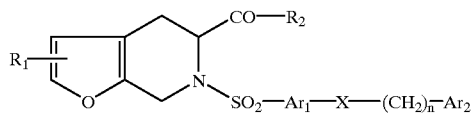

(I)

wherein:

$R_1$ represents a hydrogen or halogen atom, or a linear or branched $(C_1-C_6)$alkyl or linear or branched $(C_1-C_6)$alkoxy group, $R_2$ represents a hydroxy, linear or branched $(C_1-C_6)$alkoxy or —NHOH group, $Ar_1$ represents a phenylene or biphenylene group, X represents an oxygen or sulphur atom, an NR group, a —C≡C— group or a bond, R represents a hydrogen atom or a linear or branched $(C_1-C_6)$alkyl group, n is an integer from 0 to 6 inclusive, $Ar_2$ represents:
a phenyl group substituted by a heteroaryl group,
a biphenyl group substituted by a heteroaryl group,
a pyridinyl group substituted by a heteroaryl group, or
a heterocyclic group, their isomers and addition salts thereof with a pharmaceutically acceptable acid or base, it being understood that "heteroaryl group" is understood to mean a mono-cyclic aromatic group- or bi-cyclic aromatic group wherein at least one cycle is aromatic containing one, two or three identical or different hetero atoms selected from nitrogen, oxygen and sulphur, optionally substituted by one or more identical or different groups selected from halogen, linear or branched $(C_1-C_6)$alkyl, linear or branched $(C_1-C_6)$alkoxy, linear or branched trihalo-$(C_1-C_6)$alkyl, linear or branched trihalo-$(C_1-C_6)$alkoxy, and hydroxy, "heterocyclic group" is understood to mean a saturated or partially saturated, mono- or bi-cyclic non-aromatic group containing one, two or three identical or different hetero atoms selected from nitrogen, oxygen and sulphur, optionally substituted by one or more identical or different groups selected from halogen, linear or branched $(C_1-C_6)$alkyl, linear or branched $(C_1-C_6)$alkoxy, linear or branched trihalo-$(C_1-C_6)$alkyl, linear or branched trihalo-$(C_1-C_6)$alkoxy, and hydroxy.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases there may be mentioned by way of non-limiting example sodium hydroxide, potassium hydroxide, triethylamine, tert-butylamine, etc.

The preferred heteroaryl groups are the imidazolyl, thiazolyl, oxazolyl, pyrrolyl, pyridyl, pyrimidyl, triazolyl, pyrazolyl and benzimidazolyl groups.

The preferred heterocyclic groups are the pyrrolidinyl, morpholino, piperidino, imidazolidinyl, thiazolidinyl, oxazolidinyl, piperazinyl, isoindolyl, 2,3-dihydroisoindolyl and cyclopenta[c]pyrrolidinyl groups.

The preferred compounds of the invention are the compounds of formula (I) wherein X represents an oxygen atom or a sulphur atom.

The preferred $R_1$ group is the hydrogen atom.

The preferred $R_2$ group is the —NHOH group.

When $Ar_1$ represents a phenylene group, n is more especially zero.

When $Ar_1$ represents a phenylene group, $Ar_2$ preferably represents a phenyl group substituted by a heteroaryl group, the heteroaryl group preferably being an imidazolyl, triazolyl or pyridinyl group.

More especially, the preferred compounds of the invention are the compounds of formula (I) wherein $Ar^1$ represents a phenylene group, X represents an oxygen or sulphur atom, n is zero, and $Ar_2$ represents a phenyl group substituted by a heteroaryl group selected from imidazolyl, triazolyl and pyridinyl.

When $Ar_1$ represents a biphenylene group, $Ar_2$ preferably represents a heterocyclic group.

The configuration of the 4,5,6,7-tetrahydrofuro[2,3-c] pyridine ring is preferably (5R).

The preferred compounds of the invention are:
- 6- {4-[4-(imidazol-1-yl)phenoxy]benzenesulphonyl}-4,5, 6,7-tetrahydrofuro[2,3-c]-pyridine-(5R)-(N-hydroxy) carboxamide, and its corresponding addition salts,
- 6-{4'-[2-(pyrrolidin-1-yl)ethoxy]biphenyl-4-sulphonyl}- 4,5,6,7-tetrahydrofuro[2,3-c]-pyridine-(5R)-(N-hydroxy)carboxamide, and its corresponding addition salts,
- 6-{4-[4-(1,3,4-triazol-1-yl)phenoxy]benzenesulphonyl}- 4,5,6,7-tetrahydrofuro[2,3-c]-pyridine-(5R)-(N-hydroxy)carboxamide, and its corresponding addition salts,
- 6-{4-[4-(pyridin-4-yl)phenoxy]benzenesulphonyl}-4,5,6, 7-tetrahydrofuro[2,3-c]pyridin-(5R)-(N-hydroxy) carboxamide, and its corresponding addition salts,
- 6-{4-[(4-(1,3,4-triazol-1-yl)phenylthio] benzenesulphonyl}-4,5,6,7-tetrahydrofuro[2,3-c]- pyridine-(5R)-(N-hydroxy)carboxamide, and its corresponding addition salts.

The invention relates also to a process for the preparation of compounds of formula (I), characterised in that there is used as starting material a compound of formula (II), in racemic form or in the form of a specific isomer:

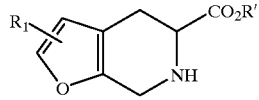
(II)

wherein $R_1$ is as defined for formula (I), and R' represents a hydrogen atom or a linear or branched $(C_1-C_6)$alkyl group, the amine function of which is substituted by a halogen compound of formula (III):

(III)

wherein $Ar_1$, X, n and $Ar_2$ are as defined for formula (I), to yield:

when R' represents a hydrogen atom, a compound of formula (I/a), a particular case of the compounds of formula (I):

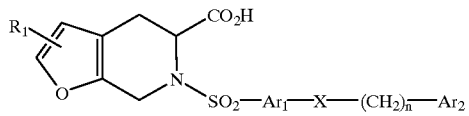
(I/a)

wherein $R_1$, $Ar_1$, X, N and $Ar_2$ are as defined hereinbefore, or, when R' represents a linear or branched $(C_1-C_6)$alkyl group (R"), a compound of formula (I/a$_1$), a particular case of the compounds of formula (I):

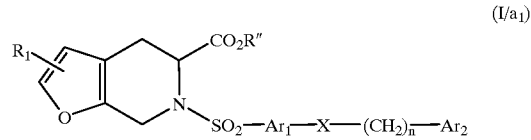
(I/a$_1$)

wherein $R_1$, $Ar_1$, X, n, $Ar_2$ and R" are as defined hereinbefore, which may be subjected to the action of an acid, to yield a compound of formula (I/a) described hereinbefore,

*which compound of formula (I/a):
is subjected, if desired, to the action of an O-substituted hydroxylamine, to yield, after deprotection of the hydroxylamine function, a compound of formula (I/b).

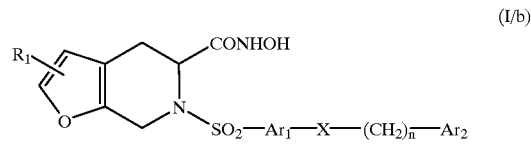
(I/b)

wherein $R_1$, $Ar_1$, X, n and $Ar_2$ are as defined hereinbefore,
*which compounds of formulae (I/a), (I/a$_1$) and (I/b) constitute the totality of the compounds of formula (I), which are purified, if necessary, according to a conventional purification technique, are separated, where appropriate, into their isomers according to a conventional separation technique, and are converted, if desired, into addition salts thereof with a pharmaceutically acceptable acid or base. The compounds of formulae (11) and (III) are either commercial products or are obtained according to known procedures.

The invention relates also to pharmaceutical compositions comprising as active ingredient one compound of formula (I) with one or more suitable inert, non-toxic excipients. Among the pharmaceutical compositions according to the invention there may be mentioned more especially those that are suitable for oral, parenteral (intravenous or subcutaneous) or nasal administration, tablets or dragees, sublingual tablets, gelatin capsules, lozenges, suppositories, creams, ointments, dermal gels, injectable preparations, drinkable suspensions, etc.

The useful dosage can be adapted according to the nature and severity of the disorder, the route of administration and according to the age and weight of the patient, and may vary from 0.01 to 2 g per day in one or more administrations.

The following Examples illustrate the invention but do not limit it in any way.

The starting materials used are known compounds or are prepared according to known procedures.

The Preparations yield synthesis intermediates for use in the preparation of the compounds of the invention.

The structures of the compounds described in the Examples and Preparations were determined according to the usual spectrophotometric techniques (infrared, NMR, mass spectrometry, etc.).

PREPARATION A

4-[4-(Imidazol-1-yl)phenoxy]benzenesulphonic acid chloride

Step A: 4-[4-(Imidazol-1-yl)phenoxy]benzenesulphonic acid 137 mmol of 1-(4-phenoxyphenyl)imidazole are dissolved in 250 ml of chloroform. 190 mmol of chlorosulphonic acid are then added dropwise. The whole is left at 45° C. overnight. After cooling and removal of the solvent by evaporation, the resulting oil is taken up in diethyl ether. The resulting solid is filtered off and dried to yield the expected product.

Melting point: 80° C.

Step B: 4-[4-(Imidazol-1-yl)phenoxy]benzenesulphonic acid chloride 80 mmol of the product described in the preceding Step and 90 mmol of $PCl_5$ are placed in 100 ml of $POCl_3$. The suspension is heated at reflux for 3 hours. After cooling, the oily residue is washed with ether and then taken up in acetonitrile. The resulting precipitate is filtered off and washed with isopropyl ether to yield the title product.

Melting point: 170° C.

PREPARATION B

4'-[2-(Pyrrolidin-1-yl)ethoxy]-biphenyl-4-sulplhonic acid chloride

Step A: 1-[2-(Biphenyloxy)ethyl]pyrrolidine 1.76 mol of 4-hydroxybiphenyl, 2.29 mol of 1-(2-chloroethyl)pyrrolidine and 5.3 mol of potassium carbonate are placed in 2.5 liters of dimethylformamide. The whole is heated at 50° C. ovemright. After cooling, the solid is filtered off and the solvent is removed by evaporation. The residue is taken up in ethyl acetate. After washing of the organic phase drying and evaporation, a residue is obtained which is purified by chromatography over silica using an ethyl acetate/ethanol mixture (80/20) as eluant. The expected product is obtained after crystallisation of the residual oil.

Step B: 4'-[2-(Pyrrolidin-1-yl)ethoxy]biphenyl-4-sulphonic acid

The expected product is obtained according to the process described in Step B of Preparation A starting from the product described in Step A.

Step C: 4'-[2-(Pyrrolidin-1-yl)etloxy]-biphenyl-4-sulphonic acid chloride

The expected product is obtained according to the process described in Step C of Preparation A starting from the compound described in Step B, maintaining reflux for 9 hours and filtering off the resulting precipitate.

Melting point: 234° C.

PREPARATION C

4'-[(Pyridin-4-yl)phenoxy]biphenyl4-sulphonic acid chloride

The expected product is obtained according to the process described in Preparation B, in Step A using 4-(4-chlorophenyl)pyridine instead of 1-(2-chloroethyl) pyrrolidine.

PREPARATION D

4'-[(2-Morpholino)etloxy]biphenyl4-sulphonic acid chloride

The expected product is obtained according to the process described in Preparation B, in Step A using 4-(2-chloroethyl) morpholine instead of 1-(2-chloroethyl)pyrrolidine.

PREPARATION E

4'-[(2-Piperidino)ethoxy]-biphenyl4-sulphonic acid chloride

The expected product is obtained according to the process described in Preparation B, in Step A using 1-(2-chloroethyl) piperidine instead of 1-(2-chloroethyl)pyrrolidine.

PREPARATION F

4'-3(Imidazol-1-yl) biphenyl-4- sulphonic acid chloride

The expected product is obtained according to the process described in Preparation B, in Step A using imidazole instead of 1-(2-chloroethyl)pyrrolidine and 4-bromobiphenyl instead of 4-hydroxybiphenyl.

PREPARATION G

4'-[4 2-(Perhydroazepind-1-yl)ethoxy]biphenyl-4-sulphonic acid chloride

The expected product is obtained according to the process described in Preparation B, in Step A using 1-(2-chloroethyl) perhydroazepine instead of 1-(2-chloroethyl)pyrrolidine.

PREPARATION H

4'-[3-(Pyrrolidin-1-yl)propoxy]biphenyl-4-sulphonic acid chloride

The expected product is obtained according to the process described in Preparation B, in Step A using 1-(3-chloropropyl)pyrroidine instead of 1-(2-chloroethyl) pyrroidine.

PREPARATION I

4'-[2-(1,3-Dihydroisoindol-2-yl)ethoxy]biphenyl4-sulphonic acid chloride

The expected product is obtained according to the process described in Preparation B, in Step A using 2-(2-chloroethyl)-1,3-dihydroisoindole instead of 1-(2-chloroethyl)pyrrolidine.

PREPARATION J

4'-[2-(Cyclopenta[c]pyrrolidin-2-yl))ehoxy] biphenyl-4-sulphonic acid chloride

The expected product is obtained according to the process described in Preparation B, in Step A using 2-(2-chloroethyl)-cyclopenta[c]pyrrolidine instead of 1-(2-chloroethyl)pyrrolidine.

PREPARATION K

4'-(Pyrrolidin-1-yl)biphenyl-4-sulphonic acid chloride

The expected product is obtained according to the process described in Preparation B in Step A using pyrrolidine instead of 1-(2-chloroethyl)pyrrolidine and 4-bromobiphenyl instead of 4-hydroxybiphenyl.

PREPARATION L

4'-(Piperidino)biphenyl-4-sulphonic acid chloride

The expected product is obtained according to the process described in Preparation B, in Step A using piperidine instead of 1-(2-chloroethyl)pyrrolidine and 4-bromobiphenyl instead of 4-hydroxybiphenyl.

PREPARATION M

4'-(Morpholino)biphenyl-4-sulphonic acid chloride

The expected product is obtained according to the process described in Preparation B, in Step A using morpholine instead of 1-(2-chloroethyl)pyrrolidine and 4-bromobiphenyl instead of 4-hydroxybiphenyl.

PREPARATION N

4'-(Cyclopenta[c]pyrrolidin-2-yl)biphenyl-4-sulphonic acid chloride

The expected product is obtained according to the process described in Preparation B, in Step A using cyclopenta[c]pyrrolidine instead of 1-(2-chloroethyl)pyrrolidine and 4-bromobiphenyl instead of 4-hydroxybiphenyl.

PREPARATION O

4'-[2-(Perhydroazepin-1-yl)ethoxy]biphenyl-4-sulphonic acid chloride

The expected product is obtained according to the process described in Preparation B, in Step A using 1,3-dihydroisoindole instead of 1-(2-chloroethyl)pyrrolidine and 4-bromobiphenyl instead of 4-hydroxybiphenyl.

PREPARATION P

4-[4-(1,3,4-Triazol-1-yl)phenoxy]benzenesulphonic acid chloride

The expected product is obtained according to the process described in Preparation A. in Step A using 1-(4-phenoxyphenyl)-1,3,4-triazole instead of 1-(4-phenoxyphenyl)imidazole.

PREPARATION Q

4-[4-(1,2,4-Triazol-1-yl)phenoxy]benzenesulphonic acid chloride

The expected product is obtained according to the process described in Preparation A, in Step A using 1-(4-phenoxyphenyl)-1,2,4-triazole instead of 1-(4-phenoxyphenyl)imidazole.

PREPARATION R

4-[4-(Pyrrol-1-yl)phenoxy]benzenesulphonic acid chloride

The expected product is obtained according to the process described in Preparation A, in Step A using 1-(4-phenoxyphenyl)pyrrole instead of 1-(4-phenoxyphenyl)imidazole.

PREPARATION S

4-[4-(Pyrazol-1-yl)phenoxy]benzenesulphonic acid chloride

The expected product is obtained according to the process described in Preparation A, in Step A using 1-(4-phenoxyphenyl)pyrazole instead of 1-(4-phenoxyphenyl)imidazole.

PREPARATION T

4-[4-(Imidazol-2-yl)phenoxy]benzenesulphonic acid chloride

The expected product is obtained according to the process described in Preparation A, in Step A using 2-(4-phenoxyphenyl)imidazole instead of 1-(4-phenoxyphenyl)imidazole.

PREPARATION U

4-[4-(Benzimidazol-1-yl)phenoxy]benzenesulphonic acid chloride

The expected product is obtained according to the process described in Preparation A, in Step A using 1-(4-phenoxyphenyl)benzimidazole instead of 1-(4-phenoxyphenyl)imidazole.

PREPARATION V

4-[4-(Pyridin-4-yl)phenoxy]benzenesulphonic acid chloride

The expected product is obtained according to the process described in Preparation A, in Step A using 4-(4-phenoxyphenyl)pyridine instead of 1-(4-phenoxyphenyl)imidazole.

PREPARATION W

4-[4-(Pyrimidin-5-yl)phenoxy]benzenesulphonic acid chloride

The expected product is obtained according to the process described in Preparation A, in Step A using 5-(4-phenoxyphenyl)pyrimidine instead of 1-(4-phenoxyphenyl)imidazole.

PREPARATION X

4-[4-(Pyrimidin-2-yl)phenoxy]benzenesulphonic acid chloride

The expected product is obtained according to the process described in Preparation A, in Step A using 2-(4-phenoxyphenyl)pyrimidine instead of 1-(4-phenoxyphenyl)imidazole.

PREPARATION Y

4-[2-(Imidazol-1-yl)pyridin-5-yl oxy]benzenesulphonic acid chloride

The expected product is obtained according to the process described in Preparation A, in Step A using 1-(5-phenoxypyridin-2-yl)imidazole instead of 1-(4-phenoxyphenyl)-imidazole.

PREPARATION Z

4-[5-(Imidazol-1-yl)pyridin-2-yloxy]benzenesulphonic acid chloride

The expected product is obtained according to the process described in Preparation A, in Step A using 1-(2-phenoxypyridin-5-yl)imidazole instead of 1-(4-phenoxyphenyl)-imidazole.

PREPARATION AA

4-[4'-(Imidazol-1-yl)biphenyl4-oxy]benzenesulphonic acid chloride

The expected product is obtained according to the process described in Preparation A, in Step A using 1-[4'-phenoxy-4-biphenyl]imidazole instead of 1-(4-phenoxyphenyl)-imidazole.

PREPARATION AB

4'-[4-(Imidazol-1-yl)phenoxy]biphenyl-4-sulphonic acid chloride

The expected product is obtained according to the process described in Preparation B, in Step A using 1-(4-chlorophenyl)-imidazole instead of 1-(2-chloroethyl)pyrrolidine.

PREPARATION AC

4-[(4-Chloropyrazol-1-yl)phenoxy]benzenesulphonic acid chloride

The expected product is obtained according to the process described in Preparation A, in Step A using 1-(4-phenoxyphenyl)-4-chloropyrazole instead of 1-(4-phenoxyphenyl)-imidazole.

PREPARATION AD

4-[4-(Imidazol-1-yl)phenylthio]benzenesulphonic acid chloride

The expected product is obtained according to the process described in Preparation A, in Step A using 1-(4-phenylthiophenyl)-imidazole instead of 1-(4-phenoxyphenyl)-imidazole.

PREPARATION AE

4-[4-(Pyridin-3-yl)phenoxy]benzenesulphonic acid chloride

The expected product is obtained according to the process described in Preparation A, in Step A using 3-(4-phenoxyphenyl)pyridine instead of 1-(4-phenoxyphenyl)-imidazole.

PREPARATION AF

4-[4-(1,3,4-Triazol-1-yl)phenylthio]benzenesulphonic acid chloride

The expected product is obtained according to the process described in Preparation A, in Step A using 1-(4-phenylthiophenyl)-1,3,4-triazole instead of 1-(4-phenoxyphenyl)-imidazole.

EXAMPLE 1

6-{4-[4-(Imidazol-1-yl)phenoxy]benzenesulphony}-4,5,6,7-tetrahydrofuro[2,3-c]pyridine-(5R)-carboxylic acid, sodium salt Step A: 6-{4-[4-(Imidazol-1-yl)phenoxy]benzenesulphonyl}-4,5,6,7-tetrahydrofuro[2,3-c]pyridine-(5R)-carboxylic acid tert-butyl ester 30 mmol of 4,5,6,7-tetrahydrofuro[2,3-c]pyridine-(5R)-carboxylic acid tert-butyl ester (obtained according to the method described by M. S. Allen, Synth. Comm., 22 (14), 207–2102, 1992) are dissolved in 60 ml of pyridine. 33 mmol of the compound described in Preparation A are then added in fractions. The mixture is stirred at room temperature overnight and then poured into 300 ml of water. After extraction with ethyl acetate, the organic phase is washed with water and then dried. After filtration and removal of the solvent by evaporation, the residue is purified by chromatography over silica gel using an ethyl acetate/pentane mixture (8/2) as eluant to yield the expected product.

Step B: 6-{-4-[4-(Imidazol-1-yl)phenoxy]benzenesulphonyl}-4,5,6,7-tetrahydrofuro[2,3-c]pyridine-(5R)-carboxylic acid, sodium salt 10 mmol of the ester obtained in Step A are dissolved in 70 ml of methylene chloride. 10 mmol of anisole are then added, followed, at 0° C., by 70 ml of trifluoroacetic acid. The reaction mixture is then stirred at room temperature overnight. After evaporation, the resulting residue is purified by chromatography over silica gel using a dichloromethane/ethanol mixture (9/1) as eluant and yields the expected product after lyophilisation of the corresponding sodium salt.

| | Elemental microanalysis: | | | |
|---|---|---|---|---|
| | C% | H% | N% | S% |
| Calculated | 56.67 | 3.72 | 8.62 | 6.58 |
| Found | 56.93 | 3.81 | 8.59 | 6.86 |

EXAMPLE 2

6-{4-[4-(Imidazol-1-yl)phenoxy]benzenesulphonyl}-4,5,6,7-tetrahydrofuro[2,3-c]pyridine-(5R)-(N-hydroxy)carboxamide hydrochloride Step A: 6-{4-[4-(Imidazolyl-1-yl)phenoxy]benzenesulphonyl}-4,5,6,7-tetrahydrofuro[2,3-c]pyridine-(5R)-(N-allyloxy)carboxamide 9 mmol of the compound described in Example 1 are dissolved in 70 ml of dichloromethane and 10 ml of dimethylformamide. There are then added to the preceding mixture 45 mmol of diisopropylethylamine, 9 mmol of dihydroxybenzotriazole, 13 mmol of O-allylhydroxylamine hydrochloride and 11 mmol of O-(benzotriazol-1-yl)-N,N,N',N'-tetramethyluronium tetrafluoroborate. After a night at room temperature, the mixture is evaporated. The residue is taken up in chloromethane. After drying, the solution is filtered and evaporated. The residue is purified by chromatography over silica gel using a dichloromethane/ethanol mixture (95/5) as eluant to yield the expected product.

Step B.: 6-{4-[4-(Imidazol-1-yl)phenoxy]benzenesulphonyl}-4,5,6,7-tetrahydrofuro[2,3-c]pyridine-(5R)-(N-hydroxy)carboxamide hydrochloride 8.5 mmol of the compound described in the preceding Step are dissolved in 120 ml of dichloromethane. 0.4 mmol of $(Ph_3P)_2PdCl_2$ and 2.5 mmol of acetic acid are added to the preceding mixture and the whole is stirred for 5 minutes before the addition of 4.8 ml of tributyltin hydride. After 5 minutes' stirring, the solvent is removed by evaporation and the residue is taken up in an acetonitrile/methanol mixture. After washing with hexane and evaporation, the residue is purified by reversed phase column chromatography using an acetonitrile/methanol mixture as eluant. After lyophilisation, the resulting solid is dissolved in acetonitrile and is converted to the corresponding hydrochloride by the addition of 4.32 ml of 1N HCl. The title product is then obtained by lyophilisation.

| | Elemental microanalysis: | | | | |
|---|---|---|---|---|---|
| | C% | H% | N% | Cl% | S% |
| Calculated | 53.44 | 4.09 | 10.84 | 6.86 | 6.20 |
| Found | 54.05 | 4.13 | 10.82 | 6.61 | 6.07 |

The following Examples were prepared according to the processes described in Example 1 or 2 starting from the corresponding starting materials.

EXAMPLE 3

6-{4'-[2-(Pyrrolidin-1-yl)ethoxy]biphenyl-4-sulphonyl}-4,5,6,7-tetrahydrofuro[2,3-c]pyridine-(5R)-carboxylic acid, sodium salt The title product is obtained according to the process described in Example 1 starting from the product described in Preparation B.

| Elemental microanalysis: | | | | |
|---|---|---|---|---|
| | C% | H% | N% | S% |
| Calculated | 55.08 | 4.79 | 4.59 | 5.25 |
| Found | 54.83 | 4.50 | 4.57 | 5.09 |

EXAMPLE 4

6-{4'-[2-(Pyrrolidin-1-yl)ethoxy]biphenyl-4-sulphonyl}-4,5,6,7-tetrahydrofuro[2,3-c]pyridine-(5R)-N-hydroxy)carboyamide hydrochloride The title product is obtained according to the process described in Example 2 starting from the product described in Example 3.

| Elemental microanalysis: | | | | | |
|---|---|---|---|---|---|
| | C% | H% | N% | Cl% | S% |
| Calculated | 56.98 | 5.52 | 7.67 | 6.47 | 5.85 |
| Found | 56.64 | 5.49 | 748 | 7.14 | 5.59 |

EXAMPLE 5

6-{4'-[4-(Pyridin-4-yl)phenoxy]biphenyl-4-sulphonyl}-4,5,6,7-tetrahydrofuro[2,3-c]pyridine-(5R)-carboxylic acid, sodium salt The title product is obtained according to the process described in Example 1 starting from the product described in Preparation C.

EXAMPLE 6

6-{4'-[4-(Pyridin4-yl)phenoy]biphenyl-4-sulphonyl}-4,5,6,7-tetrahydrofuro[2,3-c]pyridine-(5R)-(N-hydroxy)carboxamide hydrochloride The title product is obtained according to the process described in Example 2 starting from the product described in Example 5.

EXAMPLE 7

6-{4'-[2-(Morpholino)ethoxy]biphenyl-4-sulphonyl}-4,5,6,7-tetrahydrofuro[2,3-c]pyridine-(5R)-carboxylic acid, sodium salt The title product is obtained according to the process described in Example 1 starting from the product described in Preparation D.

EXAMPLE 8

6-{4'-[2-(Morpholino)ethoxy]biphenyl-4-sulphonyl}-4,5,6,7-tetrahydrofuro[2,3-c]pyridine-(5R)-(N-hydroxy)carboxamide hydrochloride The title product is obtained according to the process described in Example 2 starting from the product described in Example 7.

| Elemental microanalysis: | | | | | |
|---|---|---|---|---|---|
| | C% | H% | N% | Cl% | S% |
| Calculated | 55.36 | 5.36 | 7.45 | 6.29 | 5.68 |
| Found | 55.63 | 5.44 | 7.41 | 6.63 | 5.65 |

EXAMPLE 9

6-[4'-[2-(Piperidino)ethoxy]biphenyl-4-sulphonyl}-4,5,6,7-tetrahydrofuro[2,3-c]pyridine-(5R)-carboxylic acid, sodium salt The title product is obtained according to the process described in Example 1 starting from the product described in Preparation E.

EXAMPLE 10

6-{4'-[2-(Piperidino)ethoxy]biphenyl-4-sulphonyl}-4,5,6,7tetrahydrofuro[2,3-c]pyridine-(5R)-(N-hydroxy)carboxamide hydrochloride The title product is obtained according to the process described in Example 2 starting from the product described in Example 9.

| Elemental microanalysis: | | | | | |
|---|---|---|---|---|---|
| | C% | H% | N% | Cl% | S% |
| Calculated | 57.70 | 5.74 | 7.48 | 6.31 | 5.70 |
| Found | 57.97 | 5.79 | 7.47 | 6.54 | 5.55 |

EXAMPLE 11

6-[4'-(Imidazol-1-yl)biphenyl-4-sulphonyl]-4,5,6,7-tetrahydrofuro[2,3-c]pyridine-(5R)-carboxylic acid hydrochloride The title product is obtained according to the process described in Example 1 starting from the product described in Preparation F.

| Elemental microanalysis: | | | | | |
|---|---|---|---|---|---|
| | C% | H% | N% | Cl% | S% |
| Calculated | 56.85 | 4.15 | 8.65 | 7.30 | 6.60 |
| Found | 56.69 | 4.20 | 8.57 | 6.52 | 6.73 |

EXAMPLE 12

6-[4'-(Imidazol-1-yl)biphenyl4-sulphonyl]-4,5,6,7-tetrahydrofuro[2,3-c]Pyridine-(5R)-(N-hydroxy)carboxamide hydrochloride The title product is obtained according to the process described in Example 2 starting from the product described in Example 11.

| Elemental microanalysis: | | | | | |
|---|---|---|---|---|---|
| | C% | H% | N% | Cl% | S% |
| Calculated | 55.14 | 4.23 | 11.18 | 7.08 | 6.40 |
| Found | 55.41 | 4.18 | 11.01 | 7.27 | 6.36 |

EXAMPLE 13

6-{4'-[2-(Perhydroazepin-1-yl)ethoxy]biphenyl-4-sulphonyl}-4,5,6,7-tetrahydrofuro[2,3-c]pyridine-(5R)-carboxylic acid, sodium salt The title product is obtained according to the process described in Example 1 starting from the product described in Preparation G.

EXAMPLE 14

6-{4'-[2-(Perhydroazepin-1-yl)ethoxy]biphenyl-4-sulphonyl}-4,5,6,7-tetrahydrofuro[2,3-c]pyridine-(5R)-(N-hydroxy)carboxamide hydrochloride The title product is obtained according to the process described in Example 2 starting from the product described in Example 13.

EXAMPLE 15

6-{4'-[3-Pyrrolidin-1-ylpropoxy]biphenyl-4-sulphonyl}-4,5,6,7-tetrahydrofuro[2,3-c]pyridine-(5R)-carboxylic acid, sodium salt The title product is obtained according to the process described in Example 1 starting from the product described in Preparation H.

EXAMPLE 16

6-{4'-[3-Pyrrolidin-1-ylpropoxy]biphenyl-4-sulphonyl}-4,5,6,7-tetrahydrofuro[2,3-c]pyridine-(5R)-(N-hydroxy)carboxamide hydrochloride The title product is obtained according to the process described in Example 2 starting from the product described in Example 15.

EXAMPLE 17

6-{4'-[2-(1,3-Dihydroisoindol-2-yl)ethoxy]biphenyl-4-sulphonyl[}-4,5,6,7-tetrahydrofuro[2,3-c]pyridine-(5R)-carboxylic acid, sodium salt The title product is obtained according to the process described in Example 1 starting from the product described in Preparation I.

EXAMPLE 18

6-{4'-[2-(1,3-Dihydroisoindol-2-yl)ethoxy]biphenyl-4-sulphonyl}-4,5,6,7-tetrahydrofuro[2,3-c]pyridine-(5R)-(N-hydroxy)carboxamide hydrochloride The title product is obtained according to the process described in Example 2 starting from the product described in Example 17.

EXAMPLE 19

6-{4'-[2-(Cyclopenta[c]pyrrolidin-2-yl)ethoxy]biphenyl-4-sulphonyl}-4,5,6,7-tetrahydrofuro[2,3-c]pyridine-(5R)-carboxylic acid, sodium salt The title product is obtained according to the process described in Example 1 starting from the product described in Preparation J.

EXAMPLE 20

6-{4'-[2-(Cyclopenta[c]pyrrolidin-2-yl)ethoxy]biphentyl-4-sulphonyl}-4,5,6,7-tetrahydrofuro[2,3-c]pyridine-(5R)-(N-hydroxy)carboxamide hydrochloride The title product is obtained according to the process described in Example 2 starting from the product described in Example 19.

EXAMPLE 21

6-{4'-(Pyrrolidin-1-yl)biphenyl-4-sulphony]-4,5,6,7-tetrahydrofuro[2,3-c]pyridine-(5R)-carboxylic acid, sodium salt The title product is obtained according to the process described in Example 1 starting from the product described in Preparation K.

EXAMPLE 22

6-{4'-(Pyrrolidin-1-yl)biphenyl-4-sulphonyl]}-4,5,6,7-tetrahydrofuro[2,3-c]pyridine-(5R)-(N-hydroxy)carboxamide hydrochloride The title product is obtained according to the process described in Example 2 starting from the product described in Example 21.

EXAMPLE 23

6-{4'-(Piperidino)biphenyl-4-sulphonyl]-4,5,6,7-tetrahydrofuro[2,3-c]pyridine-(5R)-carboxylic acid, sodium salt The title product is obtained according to the process described in Example 1 starting from the product described in Preparation L.

EXAMPLE 24

6-{4'-(Piperidino)biphenyl-4-sulphonyl}-4,5,6,7-tetrahydrofuro[2,3-c]pyridine-(5R)-(N-hydroxy)carboxamide hydrochloride The title product is obtained according to the process described in Example 2 starting from the product described in Example 23.

EXAMPLE 25

6-{4'-(Morpholino)biphenyl-4-sulphonyl}-4,5,6,7-tetrahydrofuro[2,3-c]pyridine-(5R)-carboxylic acid, sodium salt The title product is obtained according to the process described in Example 1 starting from the product described in Preparation M.

EXAMPLE 26

6-{4'-(Morpholino)biphenyl4-sulphonyl}-4,5,6,7-tetralhydrofuro[2,3-c]pyridine-(5R)-(N-hydroxy)carboxamide hydrochloride The title product is obtained according to the process described in Example 2 starting from the product described in Example 25.

EXAMPLE 27

6-[4'-(Cyclopenta[c]pyrrolidin-2-yl)biphenyl-4-sulphonyl]-4,5,6,7-tetrahydrofuro[2,3-c]pyridine-(5R)-carboxylic acid, sodium salt The title product is obtained according to the process described in Example 1 starting from the product described in Preparation N.

EXAMPLE 28

6-[4'-(Cyclopenta[c]pyrrolidin-2-yl)biphenyl-4-sulphonyl]-4,5,6,7-tetrahydrofuro[2,3-c]pyridine-(5R)-(N-hydroxy)carboxamide hydrochloride The title product is obtained according to the process described in Example 2 starting from the product described in Example 27.

EXAMPLE 29

6-[4'-(1,3-Dihydroisoindol-2-yl)biphenyl-4-sulphonyl]-4,5,6,7-tetrahydrofuro[2,3-c]pyridine-(5R)-carboxylic acid, sodium salt The title product is obtained according to the process described in Example 1 starting from the product described in Preparation O.

EXAMPLE 30

6-[4'-(1,3-Dihydroisoindol-2-yl)biphenyl-4-sulphonyl]-4,5,6,7-tetrahydrofuro[2,3-c]pyridine-(5R)-(N-hydroxy)carboxamide hydrochloride The title product is obtained according to the process described in Example 2 starting from the product described in Example 29.

EXAMPLE 31

6-{4-[4-(1,3,4-Triazol-1-yl)phenoxy]benzenesulphonyl}-4,5,6,7-tetrahydrofuro[2,3-c]pyridine-(5R)-carboxylic acid, sodium salt The title product is obtained according to the process described in Example 1 starting from the product described in Preparation P.

EXAMPLE 32

6-{4-[4-(1,3,4-Triazol-1-yl)phenoxy]benzenesulphonyl}-4,5,6,7-tetrahydrofuro[2,3-c]pyridine-(5R)-(N-hydroxy)carboxamide hydrochloride The title product is obtained according to the process described in Example 2 starting from the product described in Example 31.

| Elemental microanalysis: | | | | |
|---|---|---|---|---|
| | C% | H% | N% | S% |
| Calculated | 54.88 | 3.98 | 14.55 | 6.66 |
| Found | 54.88 | 4.01 | 14.16 | 6.57 |

EXAMPLE 33

6-{4-[4-(1,2,4-Triazol-1-yl)phenoxy]benzenesulphonyl}-4,5,6,7-tetrahydrofuro[2,3-c]pyridine-(5R)-carboxylic acid, sodium salt The title product is obtained according to the process described in Example 1 starting from the product described in Preparation Q.

EXAMPLE 34

6-{4-[4-(1,2,4-Triazol-1-yl)phenoxy]benzenesulphony}-4,5,6,7-tetrahydrofuro[2,3-c]pyridine-(5R)-(N-hydroxy)carboxamide hydrochloride The title product is obtained according to the process described in Example 2 starting from the product described in Example 33.

| Elemental microanalysis: | | | | |
|---|---|---|---|---|
| | C% | H% | N% | S% |
| Calculated | 54.88 | 3.98 | 14.55 | 6.66 |
| Found | 54.77 | 4.14 | 13.70 | 6.55 |

EXAMPLE 35

6-{4-[4-(Pyrrol-1-yl)phenoxy]benzenesulphonyl}-4,5,6,7-tetrahydrofuro[2,3-c]pyridine-(5R)-carboxylic acid, sodium salt The title product is obtained according to the process described in Example 1 starting from the product described in Preparation R.

EXAMPLE 36

6-{4-[4-(Pyrrol-1-yl)phenoxy]benzenesulphonyl}-4,5,6,7-tetrahydrofuro[2,3-c]pyridine-(5R)-(N-hydroxy)carboxamide hydrochloride The title product is obtained according to the process described in Example 2 starting from the product described in Example 35.

EXAMPLE 37

6-{4-[4-(Pyrazol-1-yl)phenoxy]benzenesulphonyl}-4,5,6,7-tetrahydrofuro[2,3-c]pyridine-(5R)-carboxylic acid, sodium salt The title product is obtained according to the process described in Example 1 starting from the product described in Preparation S.

EXAMPLE 38

6-{4-[4-(Pyrazol-1-yl)phenoxy]benzenesulphonyl}-4,5,6,7-tetrahydrofuro[2,3-c]pyridine-(5R)-(N-hydroxy)carboxamide hydrochloride The title product is obtained according to the process described in Example 2 starting from the product described in Example 37.

EXAMPLE 39

6-{4-[4-(Imidazol-2-yl)phenoxy]benzenesulphonyl}-4,5,6,7-tetrahydrofuro[2,3-c]pyridine-(5R)-carboxylic acid, sodium salt The title product is obtained according to the process described in Example 1 starting from the product described in Preparation T.

EXAMPLE 40

6-{4-[4-(Imidazol-2-yl)phenoxy]benzenesulphonyl}-4,5,6,7-tetrahydrofuro[2,3-c]pyridinie-(5R)-(N-hydroxy)carboxamide hydrochloride The title product is obtained according to the process described in Example 2 starting from the product described in Example 39.

EXAMPLE 41

6-{4-[4-(Benzimidazol-1-yl)phenoxy]benzenesulphonyl}-4,5,6,7-tetrahydrofuro[2,3-c]pyridine-(5R)-carboxylic acid, sodium salt The title product is obtained according to the process described in Example 1 starting from the product described in Preparation U.

EXAMPLE 42

6-{4-[4-(Benzimidazol-1-yl)phenoxy]
benzenesulphonyl}-4,5,6,7-tetrahydrofuro[2,3-c]
pyridine-(5R)-(N-hydroxy)carboxamide
hydrochloride The title product is obtained according to the process described in Example 2 starting from the product described in Example 41.

Elemental microanalysis:

| | C % | H % | N % | Cl % | S % |
|---|---|---|---|---|---|
| Calculated | 57.19 | 4.09 | 9.88 | 6.25 | 5.65 |
| Found | 57.31 | 4.10 | 9.86 | 5.61 | 5.66 |

EXAMPLE 43

6-{4-[4-(Pyridin-4-yl)phenoxy]benzenesulpbonyl}-
4,5,6,7-tetrahydrofuro[2,3-c]pyridine-(5R)-
carboxylic acid, sodium salt The title product is obtained according to the process described in Example 1 starting from the product described in Preparation V.

EXAMPLE 44

6-{4-[4-(Pyridin-4-yl)phenoxy]benzenesulphonyl}-
4,5,6,7-tetrahydrofuro[2,3-c]pyridine-(5R)-(N-
hydroxy)carboxamide hydrochloride The title product is obtained according to the process described in Example 2 starting from the product described in Example 43.

EXAMPLE 45

6-{4-[4-(Pyrimidin-5-yl)phenoxy]
benzenesulphonyl}-4,5,6,7-tetrahydrofuro[2,3-c]
pyridine-(5R)-carboxylic acid, sodium salt The title product is obtained according to the process described in Example 1 starting from the product described in Preparation W.

EXAMPLE 46

6-{4-[4-(Pyrimidin-5-yl)phenoxy]
benzenesulphonyl}-4,5,6,7-tetrahydrofuro[2,3-c]
pyridine-(5R)-(N-hydroxy)carboxamide
hydrochloride The title product is obtained according to the process described in Example 2 starting from the product described in Example 45.

Elemental microanalysis:

| | C % | H % | N % | S % | Cl % |
|---|---|---|---|---|---|
| Calculated | 54.50 | 4.00 | 10.59 | 6.06 | 6.70 |
| Found | 54.90 | 4.13 | 10.28 | 5.74 | 6.73 |

EXAMPLE 47

6-{4-[4-(Pyrimidin-2-yl)phenoxy]
benzenesulphonyl}-4,5,6,7-tetrahydrofuro[2,3-c]
pyridine-(5R)-carboxylic acid, sodium salt The title product is obtained according to the process described in Example 1 starting from the product described in Preparation X.

EXAMPLE 48

6-{4-[4-(Pyrimidin-2-yl)phenoxy]
benzenesulphonyl}-4,5,6,7-tetrahydrofuro[2,3-c]
pyridine-(5R)-(N-hydroxy)carboxamide
hydrochloride The title product is obtained according to the process described in Example 2 starting from the product described in Example 47.

EXAMPLE 49

6-{4-[2-(Imidazol-1-yl)pyridin-5-yl oxy]
benzenesulphonyl}-4,5,6,7-tetrahydrofuro[2,3-c]
pyridine-(5R)-carboxylic acid, sodium salt The title product is obtained according to the process described in Example 1 starting from the product described in Preparation Y.

EXAMPLE 50

6-{4-[2-(Imidazol-1-yl)pyridin-5-yloxy]
benzenesulphonyl}-4,5,6,7-tetrahydrofuro[2,3-c]
pyridine-(5R)-(N-hydroxy)carboxamide
hydrochloride The title product is obtained according to the process described in Example 2 starting from the product described in Example 49.

EXAMPLE 51

6-{4-[5-(Imidazol-1-yl)pyridin-2-yloxy]
benzenesulphonyl}-4,5,6,7-tetrahydrofuro[2,3-c]
pyridine-(5R)-carboxylic acid, sodium salt The title product is obtained according to the process described in Example 1 starting from the product described in Preparation Z.

EXAMPLE 52

6-{4-[5-(Imidazol-1-yl)pyridin-2-yloxy]
benzenesulphonyl}-4,5,6,7-tetrahydrofuro[2,3-c]
pyridine-(5R)-(N-hydroxy)carboxamide
hydrochloride The title product is obtained according to the process described in Example 2 starting from the product described in Example 51.

EXAMPLE 53

6-{4-[4'-(Imidazol-1-yl)biphenyl-4-oxy]
benzenesulphonyl}-4,5,6,7-tetrahydrofuro[2,3-c]
pyridine-(5R)-carboxylic acid, sodium salt The title product is obtained according to the process described in Example 1 starting from the product described in Preparation AA.

EXAMPLE 54

6-{4-[4'-(Imidazol-1-yl)biphenyl-4-oxy]
benzenesulphonyl}-4,5,6,7-tetrahydrofuro[2,3-c]
pyridine-(5R)-(N-hydroxy)carboxamide
hydrochloride The title product is obtained according to the process described in Example 2 starting from the product described in Example 53.

| Elemental microanalysis: | | | | | |
|---|---|---|---|---|---|
| | C % | H % | N % | S % | Cl % |
| Calculated | 58.73 | 4.25 | 9.45 | 5.41 | 5.98 |
| Found | 59.09 | 4.27 | 9.23 | 5.21 | 5.97 |

EXAMPLE 55

6-{4'-[4-(Imidazol-1-yl)phenoxy]biphenyl-4-sulphonyl}-4,5,6,7-tetrahydrofuro[2,3-c]pyridine-(5R)-carboxylic acid, sodium salt The title product is obtained according to the process described in Example 1 starting from the product described in Preparation AB.

EXAMPLE 56

6-{4'-[4-(Imidazol-1-yl)phenoxy]biphenyl-4-sulphonyl}-4,5,6,7-tetrahydrofuro[2,3-c]pyridine-(5R)-(N-hydroxy)carboxamide hydrochloride The title product is obtained according to the process described in Example 2 starting from the product described in Example 55.

EXAMPLE 57

6-{4-[4-(4-Chloropyrazol-1-yl)phenoxy]benzenesulphonyl}-4,5,6,7-tetrahydrofuro[2,3-c]pyridine-(5R)-carboxylic acid, sodium salt The title product is obtained according to the process described in Example 1 starting from the product described in Preparation AC.

EXAMPLE 58

6-{4-[4-Chloropyrazol-1-yl)phenoxy]benzenesulphonyl}-4,5,6,7-tetrahydrofuro[2,3-c]pyridine-(5R)-(N-hydroxy)carboxamide The title product is obtained according to the process described in Example 2 starting from the product described in Example 57.

| Elemental microanalysis: | | | | | |
|---|---|---|---|---|---|
| | C % | H % | N % | Cl % | S % |
| Calculated | 53.65 | 3.72 | 10.88 | 6.88 | 6.23 |
| Found | 53.40 | 3.81 | 10.64 | 6.88 | 6.07 |

EXAMPLE 59

6-{4-[4-(Imidazol-1-yl)phenylthio]benzenesulphonyl}-4,5,6,7-tetrahydrofuro[2,3-c]pyridine-(5R)-carboxylic acid, sodium salt The title product is obtained according to the process described in Example 1 starting from the product described in Preparation AD

EXAMPLE 60

6-{4-(Imidazol-1-yl)phenylthio]benzenesulphonyl}-4,5,6,7-tetrahydrofuro[2,3-c]pyridine-(5R)-(N-hydroxy)carboxamide hydrochloride The title product is obtained according to the process described in Example 2 starting from the product described in Example 59.

| Elemental microanalysis: | | | | | |
|---|---|---|---|---|---|
| | C % | H % | N % | S % | Cl % |
| Calculated | 51.83 | 3.97 | 10.51 | 12.03 | 6.65 |
| Found | 51.04 | 3.99 | 10.11 | 12.26 | 7.65 |

EXAMPLE 61

6-{4-(Pyridin-3-yl)phenoxy)benzenesulphonyl}-4,5,6,7-tetrahydrofuro[2,3-c]pyridine-(5R)-carboxyic acid, sodium salt The title product is obtained according to the process described in Example 1 starting from the product described in Preparation AE.

EXAMPLE 62

6-{4-(Pyridin-3-yl)phenoxy)benzenesulphonyl}-4,5,6,7-tetrahydrofuro[2,3-c]pyridine-(5R)-(N-hydroxy)carboxamide hydrochloride The title product is obtained according to the process described in Example 2 starting from the product described in Example 61.

| Elemental microanalysis: | | | | | |
|---|---|---|---|---|---|
| | C % | H % | N % | S % | Cl % |
| Calculated | 56.87 | 4.20 | 7.96 | 6.07 | 6.71 |
| Found | 56.88 | 4.35 | 8.06 | 5.94 | 7.22 |

EXAMPLE 63

6-{4-[4-(1,3,4-Triazol-1-yl)phenylthio]benzenesulphonyl}-4,5,6,7-tetrahydrofuro[2,3-c]pyridine-(5R)-carboxylic acid, sodium salt The title product is obtained according to the process described in Example 1 starting from the product described in Preparation AF.

EXAMPLE 64

6-{4-[(4-(1,3,4-Triazol-1-yl)phenylthio]benzenesulphonyl}-4,5,6,7-tetrahydrofuro[2,3-c]pyridine-(5R)-N-hydroxy)carboxamide hydrochloride The title product is obtained according to the process described in Example 2 starting from the product described in Example 63.

EXAMPLE 65

6-{4-[4-(Imidazol-1-yl)phenoxy]benzenesulphonyl}-4,5,6,7-tetrahydrofuro[2,3-c]pyridine-(5R)-carboxylic acid ethyl ester, hydrochloride The expected product is obtained according to the process described in Step A of Example 1 starting from 4,5,6,7-tetrahydrofuro[2,3-c]pyridine-(5R)-carboxylic acid ethyl ester and the product described in Preparation A.

| Elemental microanalysis: | | | | | |
|---|---|---|---|---|---|
| | C % | H % | N % | Cl % | S % |
| Calculated | 56.66 | 4.56 | 7.96 | 6.69 | 6.05 |
| Found | 56.80 | 4.67 | 7.94 | 6.88 | 5.87 |

Pharmacological Study of the Compounds of the Invention

EXAMPLE A

Enzymatic Inhibition of Metalloproteases

Six recombinant human enzymes, MMP-1 (interstitial collagenase), MMP-2 (gelatinase A), MMP-3 (stromelysin 1), MMP-8 (neutrophil collagenase), MMP-9 (gelatinase B) and MMP-13 (collagenase 3) are activated with APMA (4-aminophenylmercuric acetate). The enzymatic tests on MMP-1, -2, -8, -9 and -13 are carried out using the following peptidomimetic substrate:

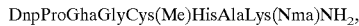

which is cleaved between the glycine and the cysteine to yield a fluorescent product described by D. M. BICKETT et al. (Anal. Biochem., 212, 58–64, 1993). The enzymatic test on MMP-3 is carried out using the following peptidomimetic substrate:

which is cleaved between alanine and norvaline to yield a fluorescent product described by H. NAGASE et al. (J. Biol. Chem., 269, 20952–20957, 1994). The reactions, carried out in a buffer of 50 mM Tris, 200 mM NaCl, 5 mM $CaCl_2$, 0.1% Brij 35 at pH 7.7, are initiated using 20 $\mu$M substrate in a total volume of 100 $\mu$l at 37° C. The fluorescence obtained after six hours is read in a 96-well plate in a fluorimeter equipped with a combination of 360 nm and 460 nm filters for excitation and emission. The compounds of the invention exhibited $IC_{50}$ values of from $10^{-10}$ to $10^{-8}$M for all of the MMPs with the exception of MMP-1. The collagenases MMP-13 and MMP-8 exhibit a specificity of a factor of 1000 compared with collagenase MMP-1.

EXAMPLE B

In Vitro Degradation of the Cartilage Matrix

The compounds of the invention were studied in a model of damage to the cartilage matrix induced by IL-1β. The test, carried out on rabbit cartilage, relates:
- on the one hand, to the degradation of collagen : colorimetric measurement according to the technique of Grant (GRANT R. A. Estimation of OH-proline by the autoanalyser, J. Clin. Path., 17, 685, 1964), of the OH-proline fraction released by the tissue in contact with IL-1β (10 ng/ml) and plasmin (0.1 U/ml) for 2 days;
- on the other hand, to the degradation of proteoglycans : radio-isotopic measurement of the fraction of glycosaminoglycans released after 24 hours' stimulation with IL-1β, (10 ng/ml) by the tissue pre-labelled with $^{35}SO_4$, over the course of 24 hours in contact with APMA ($5 \times 10^{-4}$M). The compounds of the invention were studied by addition to the culture medium for the 3 days of the test. For concentrations of from $10^{-8}$ to $10^{-6}$M, they strongly inhibited the degradation of collagen and of proteoglycans. By way of example, the activities of some of the compounds of the invention are as follows:

| | % protection at $10^{-7}$ M | |
|---|---|---|
| | Collagen | proteoglycans |
| Example 2 | 82% | 83% |
| Example 4 | 34% | 70% |
| Example 8 | 62% | 77% |
| Example 10 | 39% | 73% |
| Example 12 | 27% | 71% |
| Example 32 | 84% | 86% |
| Example 34 | 84% | 93% |
| Example 42 | 65% | 83% |
| Example 44 | 96% | 82% |
| Example 46 | 87% | 93% |
| Example 54 | 56% | 72% |
| Example 58 | 67% | 60% |
| Example 60 | 65% | 81% |

EXAMPLE C

In Vitro Angiogenesis

Portions of thoracic aorta of male Fischer 344 rats aged from 8 to 12 weeks are immersed in a type I collagen gel according to the method of Nicosia and Ottinetti (1990). After five days of culture in a medium without serum, the preparations are examined using a microscope and the formation of pseudo-vessels is quantified in terms of vascular density after digitisation and image analysis. By way of example, the $IC_{50}$ of the compound of Example 2 is 2.3 nM, and that of the compound of Example 4 is 100 nM.

EXAMPLE D

Absorption After Treatment Via the Oral Route in the Mouse-Plasma Bioactivity

The absorption of the compounds was evaluated in the circulation after oral treatment in the mouse (CD 1, male, 25–30 g) by measuring the potential of the plasma to inhibit MMP-13 under experimental conditions identical to those used in vitro (Example A). Bioactivity was determined on plasma, after elimination of the proteins by ethyl alcohol (18 h at −20° C.), at various times after administration of the compounds. By way of example, the % inhibition of MMP-13 obtained after 30 mg/kg are as follows:

| | % protection MMP-13 - 30 mg/kg p.o. | | |
|---|---|---|---|
| | 30 min | 2 h | 8 h |
| Example 2 | 88% | 83% | 51% |
| Example 4 | 91% | 94% | 68% |
| Example 8 | 92% | 72% | 76% |

EXAMPLE E

Arthritis with Freund's Adjuvant in the Rat- Protection Against Articular Degradation The protective activity of the compounds against degradation of articular tissue was studied in the model of arthritis with Freund's adjuvant in the rat (Lewis, female, 62 days). The autoimmune pathology induced by an intraplantar injection of 0.1 ml of adjuvant (Mycobacterium butyricum 4 mg/ml) in one of the rear paws, causes articular damage in addition to an inflammatory reaction. After 21 days, the damage to the paw that had not received an injection was evaluated in terms of the bones (densitometric measurement of the proximal portion of the femur) and of the patellar cartilage (OH-proline and glycosaminoglycan contents measured according to the technique of Farndale et al. (Biophysica Acta, 1986, 883, 173–177) and that described by Grant (J. Clin. Path., 1964, 17, 685), respectively). By way of example, the compound of Example 2 administered orally twice daily at a dose of 40 mg/kg (10 animals/group) caused a reduction in the loss of bone mineral content in the proximal femur of arthritic control animals by 42% (P<0.01) and a reduction in the loss of glycosaminoglycans and OH-proline of the patellar cartilage by 61% (P<0.05) and 98% (P<0.01), respectively.

EXAMPLE F

Pharmaceutical Composition

| Formulation for the preparation of 1000 tablets containing a dose of 100 mg | |
| --- | --- |
| Compound of Example 2 | 100 mg |
| Hydroxypropyl cellulose | 2 g |
| Wheat starch | 10 g |
| Lactose | 100 g |
| Magnesium stearate | 3 g |
| Talc | 3 g |

What is claimed is:

1. A compound selected from those of the formula (I):

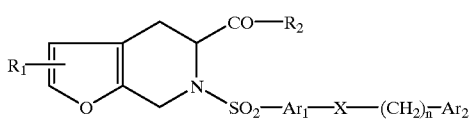

(I)

wherein:
$R_1$ represents hydrogen, halogen, linear or branched ($C_1$–$C_6$)alkyl, or linear or branched ($C_1$–$C_6$)alkoxy,
$R_2$ represents hydroxy, linear or branched ($C_{1-6}$)alkoxyl, or —NHOH,
$Ar_1$ represents phenylene or biphenylene,
X represents oxygen, sulphur, NR, —C≡C—, or a bond,
R represents hydrogen or linear or branched ($C_1$–$C_6$) alkyl,
n is 0 to 6 inclusive,
$Ar_2$ represents:
  phenyl substituted by a heteroaryl group,
  biphenyl substituted by a heteroaryl group,
  pyridinyl substituted by a heteroaryl group, or
  a heterocyclic group,
its isomers and addition salts thereof with a pharmaceutically-acceptable acid or base, it being understood that:
"heteroaryl group" is understood to mean mono-cyclic aromatic or bi-cyclic aromatic group wherein at least one cycle is aromatic containing one, two or three identical or different hetero atoms selected from nitrogen, oxygen and sulphur, optionally substituted by one or more identical or different groups selected from halogen, linear or branched ($C_1$–$C_6$)alkyl, linear or branched ($C_1$–$C_6$)alkoxy, linear or branched trihalo-($C_1$–$C_6$)alkyl, linear or branched trihalo-($C_1$–$C_6$) alkoxy, and hydroxy,
"heterocyclic group" is understood to mean saturated or partially saturated, mono-or bi-cyclic non-aromatic group containing one, two or three identical or different hetero atoms selected from nitrogen, oxygen and sulphur, optionally substituted by one or more identical or different groups selected from halogen, linear or branched ($C_1$–$C_6$)alkyl, linear or branched ($C_1$–$C_6$) alkoxy, linear or branched trihalo-($C_1$–$C_6$)alkyl, linear or branched trihalo-($C_1$–$C_6$)alkoxy, and hydroxy.

2. A compound of claim 1, wherein X represents oxygen or sulphur.

3. A compound of claim 1, wherein $R_2$ represents —NHOH.

4. A compound of claim 1, wherein $Ar_1$ represents phenylene and n is zero.

5. A compound of claim 4, wherein $Ar_2$ represents phenyl substituted by heteroaryl.

6. A compound of claim 5, wherein $Ar_2$ represents phenyl substituted by a group selected from imidazolyl, triazolyl and pyridinyl.

7. A compound of claims 1, wherein X represents oxygen or sulphur, $R_2$ represents —NHOH, $Ar_1$ represents phenylene, n is zero, and $Ar_2$ represents phenyl substituted by a group selected from imidazolyl, triazoly, and pyridinyl.

8. A compound of claim 1, wherein $Ar_1$ represents biphenylene and $Ar_2$ represents a heterocyclic group.

9. A compound of claim 1 which is selected from 6-{4-[4-(imidazol-1-yl)phenoxy]benzenesulphonyl}-4,5,6,7-tetrahydrofuro[2,3-c]pyridine-(5R)-(N-hydroxy)-carboxamide and its isomers and addition salts thereof with a pharmaceutically-acceptable acid or base.

10. A compound of claim 1 which is selected from 6-{4'-[2-(pyrrolidin-1-yl)ethoxy]biphenyl-4-sulphonyl}-4,5,6,7-tetrahydrofuro[2,3-c]pyridine-(5R)-(N-hydroxy)-carboxamide hydrochloride and its isomers and addition salts thereof with a pharmaceutically-acceptable acid or base.

11. A compound of claim 1 which is selected from 6-{4-[4-(1,3,4-triazol-1-yl)phenoxy]benzenesulphonyl}-4,5,6,7-tetrahydrofuro[2,3-c]pyridine-(5R)-(N-hydroxy) carboxamide and its isomers and addition salts thereof with a pharmaceutically-acceptable acid or base.

12. A compound of claim 1 which is selected from 6-{4-[4-(pyridin-4-yl)-phenoxy]benzenesulphonyl}-4,5,6,7-tetrahydrofuro[2,3-c]pyridine-(5R)-(N-hydroxy)-carboxamide and its isomers and addition salts thereof with a pharmaceutically-acceptable acid or base.

13. A compound of claim 1 which is selected from 6-{4-[(4-(1,3,4-triazol-1-yl)phenylthio]benzenesulphonyl}-4,5,6,7-tetrahydrofuro[2,3-c]pyridine-(5R)-(N-hydroxy)-carboxamide and its isomers and addition salts thereof with a pharmaceutically-acceptable acid or base.

14. A method for treating living animal body afflicted with a condition requiring a metalloprotease inhibitor comprising the step of administering to the living body an amount of a compound of claim I which is effective for alleviation of said condition.

15. A pharmaceutical composition useful as a metalloprotase inhibitor comprising as active principle an effective amount of a compound as claimed in claim 1, together with one or more pharmaceutically-acceptable excipients or vehicles.

* * * * *